(12) United States Patent
Dairiki et al.

(10) Patent No.: US 8,163,674 B2
(45) Date of Patent: Apr. 24, 2012

(54) AGRICULTURAL CHEMICAL COMPOSITION IN GRANULAR FORM

(75) Inventors: Hiroshi Dairiki, Shizuoka (JP); Seizo Hashimoto, Kanagawa (JP)

(73) Assignee: Nippon Soda Co., Ltd., Tokyo (JP)

( * ) Notice: Subject to any disclaimer, the term of this patent is extended or adjusted under 35 U.S.C. 154(b) by 406 days.

(21) Appl. No.: 10/523,106

(22) PCT Filed: Aug. 6, 2003

(86) PCT No.: PCT/JP03/10000
§ 371 (c)(1),
(2), (4) Date: Feb. 3, 2005

(87) PCT Pub. No.: WO2004/014136
PCT Pub. Date: Feb. 19, 2004

(65) Prior Publication Data
US 2006/0035787 A1    Feb. 16, 2006

(30) Foreign Application Priority Data
Aug. 7, 2002    (JP) ................................ 2002-229632

(51) Int. Cl.
*A01N 25/12*    (2006.01)
(52) U.S. Cl. ..................................... 504/367; 504/116.1
(58) Field of Classification Search ............... 504/116.1, 504/367
See application file for complete search history.

(56) References Cited

U.S. PATENT DOCUMENTS

| | | | |
|---|---|---|---|
| 4,739,040 A | 4/1988 | Naae et al. | |
| 4,755,186 A | 7/1988 | Ernst | |
| 5,043,432 A * | 8/1991 | Dilling | 530/500 |
| 5,180,420 A * | 1/1993 | Katayama et al. | 504/367 |
| 5,354,742 A * | 10/1994 | Deming et al. | 514/117 |
| 5,980,926 A * | 11/1999 | Suzuki et al. | 424/405 |
| 5,981,433 A * | 11/1999 | Bramati et al. | 504/364 |
| 6,774,087 B1* | 8/2004 | Nakayama et al. | 504/273 |
| 6,855,327 B1* | 2/2005 | Lundstedt | 424/405 |
| 2003/0036481 A1* | 2/2003 | Suzuki | 504/367 |
| 2004/0102323 A1 | 5/2004 | Vigil et al. | |

FOREIGN PATENT DOCUMENTS

| | | |
|---|---|---|
| DE | 3434353 | 3/1986 |
| EP | 0224092 | 6/1987 |
| EP | 1157612 A1 | 11/2001 |
| JP | 62-263101 | 11/1987 |
| JP | 3-128301 | 5/1991 |
| JP | H4-252294 | 9/1992 |
| JP | 05-43402 | 2/1993 |
| JP | 05-043402 * | 2/1993 |
| JP | 7-17810 | 1/1995 |
| JP | 8-34702 | 2/1996 |
| JP | 9-183704 | 7/1997 |
| JP | 11-49604 | 2/1999 |
| WO | WO 00/53688 | 9/2000 |
| WO | WO 01/47355 * | 7/2001 |

OTHER PUBLICATIONS

Erdman, H. et al., "Studies on the sulfonation of Lignin. II. Sulfonation of ethoxylated lignosulfonic acids of low sulfur content," Acta Chemica Scandinavica, 1950, V. 4, pp. 971-977.

* cited by examiner

*Primary Examiner* — Rebecca Prouty
*Assistant Examiner* — Danielle Sullivan
(74) *Attorney, Agent, or Firm* — Paul E. White, Jr.; Manelli Selter PLLC

(57) ABSTRACT

The present invention provides a granulated pesticidal composition comprising a pesticidal active ingredient, a lignosulfonate surfactant with a degree of sulfonation of at least 2.0, and a sulfate or phosphate salt of a polyoxyalkylene arylphenyl ether. The composition is highly dispersible in water and allows stable long-term maintenance of its properties observed immediately after preparation.

2 Claims, No Drawings

AGRICULTURAL CHEMICAL COMPOSITION IN GRANULAR FORM

This application is the national phase of international application PCT/JP03/10000 filed 6 Aug. 2003 which designated the U.S.

TECHNICAL FIELD

The present invention relates to a granulated pesticidal composition having high dispersibility in water and stability. In particular, the present invention relates to a granulated pesticidal composition comprising cyflufenamid and an EBI agent as active ingredients.

BACKGROUND ART

Among pesticides, formulations such as emulsifiable concentrates, wettable powders and flowables are intended for dilution with water for use as spray applications. Among such formulations, emulsifiable concentrates involve problems of, e.g., toxicity, irritation, flammability and bad odor because they use an organic solvent as a carrier. Likewise, due to their fine powder form, wettable powders are inconvenience in metering and are likely to affect the safety of operators because they are blown up into the air (in a process known as "dustiness") when prepared into a spray solution.

Furthermore, flowables take the form of suspension and hence overcome the problems of metering and dustiness associated with wettable powders. However, such flowable formulations are highly viscous and difficult to remove from containers, so a small portion of the formulations will remain in the containers and cause problems in disposal of the containers. To overcome the above problems, recent attempts have been made with particular regard to the granulation of wettable powders. Namely, the granulation of wettable powders allows improvements in dustiness and metering of wettable powders.

However, if conventional binders for granules are used to overcome the problem of dustiness, harder granules may generally be produced and be responsible for insufficient efficacy due to reduced dispersion in water, etc. In contrast, if an attempt is made to provide the same degree of dispersion in water as observed in wettable powders, problems of low hardness and easy powdering of granules will arise. As a result, the formulations contain more products in fine powder form and are more likely, during spraying, to cause inhalation of the fine powder products by operators and to cause powder scattering outside a target area to be sprayed, thus leading to the same problems caused when using traditional wettable powders. Although various attempts have been made to use conventional binders for granulated wettable powders, the use of such binders could not simultaneously achieve both improved powdering property and good dispersion in water.

To solve these problems, many studies have been conducted on the granulation of wettable powders. Granulated wettable powders known from these studies include:

a granulated pesticidal wettable powder comprising a pesticidal active ingredient in combination with starch and a water-soluble inorganic salt such as ammonium sulfate (JP 51-1649 A);

a water-dispersible granule capable of forming a good suspension, which comprises a plant protection agent and a specific solid wetting agent and/or an ammonium salt (JP 3-193702 A);

a water-soluble pesticidal granule comprising a water-soluble pesticidal active ingredient, lactose and a surfactant as essential ingredients (JP 6-92803 A); and a granulated wettable powder prepared by extrusion granulation of a novel composition comprising a pesticidal active ingredient and diatomaceous earth, and preferably further comprising a surfactant (JP 6-128102 A).

Likewise, solid formulations based on starch hydrolysate include:

a powdered pesticidal composition prepared by adsorbing a pesticidal active ingredient and a surfactant onto drum-dried powder of an aqueous dispersion comprising starch hydrolysate and one or more polymer materials selected from the group consisting of seaweed extract, plant seed mucilage, plant fruit mucilage, plant resinoid mucilage, microorganism-produced mucilage, water-soluble or water-dispersible proteins, cellulose derivatives and water-soluble synthetic polymers (JP 60-36402 A); and a pesticidal solid emulsion comprising a spray-dried product of an aqueous emulsion containing, as essential ingredients, a pesticidal active ingredient with a melting point of 70° C. or less, a surfactant, dextrin and/or lactose, and water (JP 3-47103 A).

Granulated pesticidal compositions incorporated with sodium lignosulfonate include:

a water-dispersible granulated pesticidal composition characterized by containing two types of surfactants, one of which is selected from lignosulfonate, a naphthalenesulfonate formaldehyde condensate and the like, and the other of which is selected from an alkylnaphthalenesulfonate, a polyoxyethylene alkylphenyl ether sulfate and the like (JP 5-43402 A);

a pesticidal composition comprising 5-ethyl-5,8-dihydro-8-oxo-1,3-dioxolo[4,5-g]quinoline-7-carboxylic acid (oxolinic acid) and N-propyl-N-[2-(2,4,6-trichlorophenoxy)ethyl]imidazole-1-carboxamide (prochloraz) dissolved in a hydrophobic organic solvent, wherein these two ingredients are dispersed or emulsified into water containing a lignosulfonate surfactant with a degree of sulfonation of 2.5 or less (JP 7-17810 A);

a (granulated) wettable powder comprising one or more pesticidal active ingredients and a highly-purified and partially-desulfonated lignosulfonate salt (JP 8-34702 A); and a granulated wettable powder comprising a pesticidal active ingredient, a lignosulfonate salt, a polyoxyethylene alkyl ether sulfate salt and a water-soluble inorganic salt (JP 2002-179506 A).

However, there is no disclosure on a composition comprising a sulfate or phosphate salt of a polyoxyalkylene arylphenyl ether in combination with highly sulfonated sodium lignosulfonate.

DISCLOSURE OF THE INVENTION

Traditional pesticidal compositions have failed to provide satisfactory results because some are rapidly dispersible in water, but are easily powdered, and others are resistant to powdering, but less dispersible in water. In particular, granulated pesticidal compositions less dispersible in water would have some problems, e.g., of providing an incomplete dispersion even after sufficient stirring, due to their poor wettability and dispersibility, or of producing too much sediment to serve as wettable powders. Moreover, their wettability and dispersibility would become poorer over time and produce even more sediment.

The object of the present invention is to provide a granulated pesticidal composition, which is resistant to powdering, which is readily wettable and dispersible in water when the pesticidal composition is added to water during the preparation of a pesticide solution, which ensures slow sedimentation, and which produces no decrease in these physical properties over time. More specifically, the present invention provides a granulated pesticidal composition comprising cyflufenamid as an active ingredient.

The present invention is directed to a granulated pesticidal composition comprising a pesticidal active ingredient(s), a lignosulfonate surfactant with a degree of sulfonation of at least 2.0, and a sulfate or phosphate salt of a polyoxyalkylene arylphenyl ether. In particular, the composition comprises cyflufenamid and triflumizole as pesticidal active ingredients.

Lignosulfonate surfactants with a low degree of sulfonation have a small number of polar sulfonate residues, and thus they may be slowly dissolved into water and be less adsorptive to solid particles for dispersing them. In contrast, lignosulfonate surfactants with a high degree of sulfonation are rapidly dissolved into water and are highly capable of dispersing solid particles through strong adsorption of sulfonate groups onto the solid surface. The combination of such a surfactant and a sulfate or phosphate salt of a polyoxyalkylene arylphenyl ether enables the stable provision of a pesticidal composition having high dispersibility.

MODE FOR CARRYING OUT THE INVENTION

As used herein, a lignosulfonate surfactant with a degree of sulfonation of at least 2.0 refers to a lignosulfonate surfactant having on average at least 2.0 (usually 2 to 6) sulfonate groups per lignin unit whose molecular weight is set to 1000. Such a lignosulfonate surfactant is usually an alkali metal (e.g., potassium, sodium) salt of lignosulfonic acid or an alkaline earth metal (e.g., calcium) salt of lignosulfonic acid, etc. Specific examples include POLYFON T (degree of sulfonation: 2.0), POLYFON F (degree of sulfonation: 4.0), REAX80C (degree of sulfonation: 2.0), REAX82 (degree of sulfonation: 2.0), REAX83A (degree of sulfonation: 2.1), REAX88B (degree of sulfonation: 3.8), REAX100M (degree of sulfonation: 4.7), REAX45DA (degree of sulfonation: 3.8), REAX45DTC (degree of sulfonation: 3.8), PC-825 (degree of sulfonation: 4.6) and PC-876A (degree of sulfonation: 2.4), which are commercially available from Westvaco.

These lignosulfonate surfactants may be incorporated alone or in combination in an amount capable of dispersing a pesticidal active ingredient(s), more specifically in an amount of 1 to 15% by weight, and preferably in an amount of 2 to 10% by weight of the composition.

A sulfate or phosphate salt of a polyoxyalkylene arylphenyl ether, as used herein, encompasses mono-, di- and tri-substituted forms having a polyoxyalkylene moiety with a polymerization degree of 2 to 50 (preferably 4 to 30) such as polyoxyethylene, polyoxypropylene or polyoxybutylene and having a $C_{6-40}$ aryl moiety such as phenyl, naphthyl or styryl. Examples of salts available for this purpose include alkali metal salts such as potassium and sodium salts, alkaline earth metal salts such as calcium and magnesium salts, ammonium salts, and alkanolamine salts such as mono-, di- and tri-ethanolamine salts.

These sulfate or phosphate salts of polyoxyalkylene arylphenyl ethers may be incorporated alone or in combination in an amount capable of dispersing a pesticidal active ingredient(s), more specifically in an amount of 0.01 to 15% by weight, and preferably in an amount of 0.5 to 10% by weight of the composition.

The granulated wettable powder of the present invention may comprise one or more pesticidal active ingredients.

Examples of fungicidal ingredients include triflumizole, tebuconazole, fenpropidin, bromuconazole, cyproconazole, difenoconazole, fenbuconazole, flusilazole, flutriafol, hexaconazole, propiconazole, tetraconazole, triadimefon, triadimenol, bitertanol, imibenconazole, diniconazole, fenpropimorph, tridemorph, epoxyconazole, fluquinconazole, prochloraz, metconazole, azoxystrobin, isoprothiolane, iprodione, iminoctadine albesilate, oxolinic acid, captan, kresoxim-methyl, diethofencarb, streptomycin, lime sulfur, dazomet, thiuram, thiophanate-methyl, triazine, pyroquilon, fluazinam, flusulfamide, procymidone, probenazole, promocarb, fosetyl, benomyl, pencycuron, mancozeb and mepanipyrim.

Examples of insecticidal ingredients include acetamiprid, acephate, imidacloprid, ethylthiometon, etoxazole, etofenprox, emamectin benzoate, chloropicrin, chlorfenapyr, fenbutatin oxide, spinosad, cycloprothrin, methyl bromide, morantel tartarate, diazinon, tralomethrin, bifenthrin, fipronil, fenpropathrin, flufenoxuron, hexythiazox, benfuracarb, milbemectin, methomyl, D-D, DDVP, DMTP and MEP.

Examples of herbicidal ingredients include ioxynil, chlorate, glyphosate isopropylamine salt, glufosinate, trifluralin, bialaphos, pretilachlor and pendimetharin.

The amount of such a pesticidal active ingredient added to the formulation is not particularly limited, but it is usually 0.01 to 90% by weight, preferably 0.1 to 60% by weight of the total formulation.

In addition to the two types of surfactants mentioned above, the composition of the present invention may comprise an additional surfactant(s), a binder(s) and/or a carrier(s).

Examples of additional surfactants include nonionic surfactants, anionic surfactants, cationic surfactants and amphoteric surfactants. Specific examples include:

nonionic surfactants such as polyoxyethylene alkyl ethers, polyoxyethylene alkylaryl ethers, polyoxyethylene styrylphenyl ether, polyoxyethylene alkyl esters, polyoxyethylene sorbitan alkylates, polyoxyethylene phenyl ether polymers, polyoxyethylene alkylenearylphenyl ethers, polyoxyethylene alkylene glycols, polyoxyethylene/polyoxypropylene block polymers and vegetable fat and oil polyoxyethylene ethers;

anionic surfactants such as alkylarylsulfonates (e.g., sodium alkylarylsulfonate, potassium alkylarylsulfonate, ammonium alkylarylsulfonate), dialkylsulfosuccinates, alkylnaphthalenesulfonates (e.g., sodium alkylnaphthalenesulfonate), polycondensates of naphthalenesulfonates with formaldehyde, and polycarboxylates;

cationic surfactants such as alkyl quaternary ammonium salts, alkylamine salts and alkylpyridinium salts; and amphoteric surfactants such as alkyl betaines and amine oxides.

Additional surfactants available for use in the present invention are not limited to those listed above and may be used alone or in combination. The amount of such an additional surfactant is not particularly limited, but it is desirably 0.1 to 30 parts by weight of the total formulation in terms of efficacy and cost.

Examples of binders available for use in the present invention include, but are not limited to, starch, dextrin, cellulose, methyl cellulose, ethyl cellulose, carboxymethyl cellulose, hydroxyethyl cellulose, hydroxypropyl cellulose, carboxymethyl starch, pullulan, sodium alginate, ammonium alginate, propylene glycol alginate, guar gum, locust bean gum, gum arabic, xanthan gum, gelatin, casein, polyvinyl alcohol, polyethylene oxide, polyethylene glycol, ethylene/propylene block polymer, sodium polyacrylate, polyvinylpyrrolidone and carrageenan.

These binders may be used alone or in combination. The amount of such a binder is not particularly limited, but it is desirably 0.1 to 40 parts by weight of the total formulation in terms of efficacy and cost.

Carriers available for use in the present invention may be either inorganic or organic. Examples of inorganic carriers include clay, bentonite, talc, calcium carbonate, calcium sulfate, sodium carbonate, zeeklite, sericite, acid clay, silica, diatomaceous earth, pumice, zeolite, vermiculite, potassium chloride, urea, white carbon, ammonium sulfate, sodium sulfate, pearlite and magnesium sulfate. Examples of organic carriers include glucose, maltose, sucrose, lactose and starch. These inorganic or organic carriers may be used alone or in combination. Of course, inorganic and organic carriers may be combined with each other.

In addition to the ingredients mentioned above, the pesticidal composition of the present invention may further comprise an auxiliary agent(s). For example, the pesticidal composition may further comprise an antiseptic and fungicidal agent and/or a solvent, as well as a stabilizer for the pesticidal active ingredient(s) including an antioxidant, a UV inhibitor and a precipitation inhibitor, if necessary. Auxiliary agents available for use in the present invention are not limited to those listed above.

Examples of solvents available for use in the present invention include polybasic acid alcohol esters such as isobutyl adipate, dioleyl adipate, diisodecyl adipate, diethylhexyl phthalate, didecyl phthalate, 2-ethylhexyl trimellitate and triisodecyl trimellitate; fatty acid alcohol esters such as cetyl 2-ethylhexanoate, coconut oil fatty acid cetyl ester, methyl laurate, methyl myristate, methyl oleate and octyl oleate; polyalcohol fatty acid esters such as sorbitan monolaurate and sorbitan monooleate; higher alcohols such as octyl alcohol and lauryl alcohol; and aromatic hydrocarbons such as 1,2-dimethyl-4-ethylbenzene, methylnaphthalene, 1-phenyl-1-xylylethane and 1-xylyl-1,3-diphenylbutane.

The pesticidal composition of the present invention may be prepared in any manner, for example, by mixing a pesticidal active ingredient(s) with surfactants, a binder and a carrier, and if necessary with an auxiliary agent (e.g., an antiseptic and fungicidal agent, a stabilizer for the pesticidal active ingredient(s)), followed by pulverization in a jet mill to give a powdered pesticidal composition.

The powdered pesticidal composition thus prepared may then be kneaded with water and granulated in an extrusion granulator, followed by drying and size selection. Alternatively, it may be granulated in a tumbling granulator while supplying water, followed by drying and size selection. Also, the wettable pesticidal composition in powder form may be dispersed in water and granulated in a spray granulator, or may be directly granulated in a fluid-bed granulator where the powder mixture is fluidized and sprayed with a binder solution or a pesticidal active ingredient(s), etc. The granulated pesticidal composition of the present invention has substantially the same particle size as conventional granulated formulations. More specifically, it is designed to have a desirable particle size ranging from 0.1 to 2 mm.

The pesticidal composition of the present invention may be formulated into, but not limited to, powder, granules or an aqueous suspension.

EXAMPLES

The present invention will be further described in the following Examples, which are not intended to limit the scope of the invention. All parts are parts by weight in the following Examples.

Example 1

Cyflufenamid (3.7 parts), triflumizole (16.6 parts), sodium dodecylbenzenesulfonate (0.35 parts), anhydrous sodium sulfate (0.15 parts), urea (1 part), potassium chloride (10 parts), clay (61.2 parts), sodium lignosulfonate with a degree of sulfonation of 4.7 (5.25 parts, REAX100M, Westvaco) and polyoxyethylene (polymerization degree: 9) tristyrylphenyl ether sulfate ammonium salt (1.75 parts) were mixed and pulverized in a jet mill (trade name: Ulmax, Nisso Engineering, Co., Ltd.). The ingredients thus pulverized were then kneaded with water (25 parts) and extrusion-granulated using a 0.7 mm screen. The resulting granules were dried at 40° C. for 24 hours and screened to collect the fraction remaining between 0.59 and 0.84 mm meshes, thereby giving a granulated pesticidal composition.

Example 2

The same procedure as shown in Example 1 was repeated to give a granulated pesticidal composition, except that the amount of clay was changed from 61.2 parts to 60.2 parts, the amount of sodium lignosulfonate was changed from 5.25 parts to 6 parts, and the amount of polyoxyethylene tristyrylphenyl ether sulfate ammonium salt was changed from 1.75 parts to 2 parts.

Example 3

The same procedure as shown in Example 1 was repeated to give a granulated pesticidal composition, except that the amount of clay was changed from 61.2 parts to 59.2 parts, the amount of sodium lignosulfonate was changed from 5.25 parts to 6.75 parts, and the amount of polyoxyethylene tristyrylphenyl ether sulfate ammonium salt was changed from 1.75 parts to 2.25 parts.

Example 4

The same procedure as shown in Example 1 was repeated to give a granulated pesticidal composition, except that the amount of clay was changed from 61.2 parts to 58.2 parts, the amount of sodium lignosulfonate was changed from 5.25 parts to 7.5 parts, and the amount of polyoxyethylene tristyrylphenyl ether sulfate ammonium salt was changed from 1.75 parts to 2.5 parts.

Example 5

The same procedure as shown in Example 1 was repeated to give a granulated pesticidal composition, except that sodium dodecylbenzenesulfonate used in Example 4 was replaced by sodium alkylnaphthalenesulfonate.

Example 6

The same procedure as shown in Example 1 was repeated to give a granulated pesticidal composition, except that sodium lignosulfonate with a degree of sulfonation of 4.7 used in Example 1 was replaced by sodium lignosulfonate with a degree of sulfonation of 4.0 (POLYFON-F, Westvaco).

Example 7

The same procedure as shown in Example 1 was repeated to give a granulated pesticidal composition, except that polyoxyethylene (polymerization degree: 9) tristyrylphenyl ether sulfate ammonium salt used in Example 2 was replaced by polyoxyethylene (polymerization degree: 14) tristyrylphenyl ether sulfate ammonium salt.

Example 8

The same procedure as shown in Example 1 was repeated to give a granulated pesticidal composition, except that polyoxyethylene (polymerization degree: 9) tristyrylphenyl ether sulfate ammonium salt used in Example 2 was replaced by polyoxyethylene (polymerization degree: 7) tristyrylphenyl ether sulfate ammonium salt.

Example 9

The same procedure as shown in Example 1 was repeated to give a granulated pesticidal composition, except that polyoxyethylene (polymerization degree: 9) tristyrylphenyl ether sulfate ammonium salt used in Example 2 was replaced by polyoxyethylene (polymerization degree: 4) tristyrylphenyl ether sulfate ammonium salt.

Example 10

The same procedure as shown in Example 1 was repeated to give a granulated pesticidal composition, except that cyflufenamid used in Example 2 was replaced by clay.

Example 11

The same procedure as shown in Example 1 was repeated to give a granulated pesticidal composition, except that polyoxyethylene (polymerization degree: 9) tristyrylphenyl ether sulfate ammonium salt used in Example 2 was replaced by polyoxyethylene (polymerization degree: 14) tristyrylphenyl ether phosphate potassium salt.

Example 12

The same procedure as shown in Example 1 was repeated to give a granulated pesticidal composition, except that sodium lignosulfonate with a degree of sulfonation of 4.7 used in Example 1 was replaced by sodium lignosulfonate with a degree of sulfonation of 2.0 (POLYFON-T, Westvaco).

Comparative Example 1

The same procedure as shown in Example 1 was repeated to give a granulated pesticidal composition, except that the amount of clay was changed from 61.2 parts to 54.2 parts, sodium lignosulfonate with a degree of sulfonation of 4.7 (5.25 parts) was replaced by sodium lignosulfonate with a degree of sulfonation of 0.5 (14 parts, POLYFON-H, Westvaco), sodium dodecylbenzenesulfonate was replaced by sodium alkylnaphthalenesulfonate, and the amount of polyoxyethylene tristyrylphenyl ether sulfate ammonium salt was changed from 1.75 parts to 0 parts.

Comparative Example 2

The same procedure as shown in Example 1 was repeated to give a granulated pesticidal composition, except that potassium chloride used in Comparative Example 1 was replaced by sodium chloride.

Comparative Example 3

The same procedure as shown in Example 1 was repeated to give a granulated pesticidal composition, except that sodium lignosulfonate with a degree of sulfonation of 0.5 used in Comparative Example 1 was replaced by sodium lignosulfonate with a degree of sulfonation of 1.7 (REAX910, Westvaco).

Comparative Example 4

The same procedure as shown in Example 1 was repeated to give a granulated pesticidal composition, except that potassium chloride (10 parts) used in Comparative Example 3 was replaced by potassium chloride (5 parts) and calcined diatomaceous earth (5 parts).

Comparative Example 5

The same procedure as shown in Example 1 was repeated to give a granulated pesticidal composition, except that sodium lignosulfonate (6 parts) and polyoxyethylene tristyrylphenyl ether sulfate ammonium salt (2 parts) used in Example 2 were replaced by sodium polycarboxylate (8 parts, Geropon T-36, Rhodia Nicca, Ltd.).

Comparative Example 6

The same procedure as shown in Example 1 was repeated to give a granulated pesticidal composition, except that sodium polycarboxylate used in Comparative Example 5 was replaced by sodium lignosulfonate with a degree of sulfonation of 4.7 as used in Example 1.

Comparative Example 7

The same procedure as shown in Example 1 was repeated to give a granulated pesticidal composition, except that sodium polycarboxylate used in Comparative Example 5 was replaced by sodium lignosulfonate with a degree of sulfonation of 4.0 as used in Example 6.

Comparative Example 8

The same procedure as shown in Example 1 was repeated to give a granulated pesticidal composition, except that sodium polycarboxylate used in Comparative Example 5 was replaced by sodium lignosulfonate with a degree of sulfonation of 1.7 as used in Comparative Example 3.

Comparative Example 9

The same procedure as shown in Example 1 was repeated to give a granulated pesticidal composition, except that sodium polycarboxylate used in Comparative Example 5 was replaced by sodium lignosulfonate with a degree of sulfonation of 1.2 (POLYFON-O, Westvaco).

Comparative Example 10

The same procedure as shown in Example 1 was repeated to give a granulated pesticidal composition, except that sodium polycarboxylate used in Comparative Example 5 was replaced by sodium lignosulfonate with a degree of sulfonation of 0.5 as used in Comparative Example 1.

Comparative Example 11

The same procedure as shown in Example 1 was repeated to give a granulated pesticidal composition, except that sodium lignosulfonate with a degree of sulfonation of 4.7 used in Example 2 was replaced by sodium lignosulfonate with a degree of sulfonation of 0.5 as used in Comparative Example 1.

Comparative Example 12

The same procedure as shown in Example 1 was repeated to give a granulated pesticidal composition, except that sodium lignosulfonate with a degree of sulfonation of 4.7 used in Example 2 was replaced by sodium lignosulfonate with a degree of sulfonation of 1.2 (POLYFON-O, Westvaco).

Comparative Example 13

The same procedure as shown in Example 1 was repeated to give a granulated pesticidal composition, except that cyflufenamid used in Comparative Example 12 was replaced by clay.

Test Example 1

Measurement of Dilution Properties

Test tubes were provided, each of which, when changed with 100 mL of water, would form a water column measuring about 180 mm high from the bottom and leaving an open space of 30 mL at the top. The pesticidal compositions prepared in the Examples and Comparative Examples (100 mg each) were slowly added into the test tubes and measured for the following properties: (i) self-dispersibility, (ii) the number of tube inversions required for dispersion in water, and (iii) sediment volume, using the procedure and criteria shown below.

Table 1 shows the results obtained.

(i) Self-Dispersibility

The pesticidal compositions according to the present invention were slowly added to distilled water in the tubes and monitored for dispersion until they reached the bottom, followed by evaluation under the following criteria:

◎: a test composition substantially disperses before reaching the bottom;

○: a test composition starts to disperse before reaching a depth of about 90 mm from the surface;

Δ: a test composition does not start to disperse before reaching a depth of about 90 mm from the surface, but it starts to disperse before reaching the bottom; and X: a test composition does not disperse at all before reaching the bottom.

(ii) Number of Tube Inversions Required for Dispersion in Water

Thirty seconds after the pesticidal compositions according to the present invention were slowly added to distilled water, the test tubes were inverted repeatedly at a rate of once per 2 seconds to measure the number of tube inversions required for complete dispersion of each composition.

(iii) Sediment Volume

After measuring the number of tube inversions required for dispersion in water, an additional 30 times of tube inversions were repeated at a rate of once per 2 seconds and the sediment volume (mL) was measured for each tube after 30 minutes.

TABLE 1

| | Immediately after preparation | | | After standing at 54° C. for 14 days | | |
|---|---|---|---|---|---|---|
| | Self-dispersibility | Number of tube inversions | Sediment volume (30 min) | Self-dispersibility | Number of tube inversions | Sediment volume (30 min) |
| Example 1 | ○ | 2 | 0.01 | ○ | 4 | 0.01 |
| Example 2 | ○ | 2 | 0.01 | ○ | 4 | 0.01 |
| Example 3 | ○ | 2 | 0.01 | ○ | 4 | <0.01 |
| Example 4 | ○ | 3 | 0.01 | ○ | 5 | <0.01 |
| Example 5 | ○ | 4 | 0.01 | ○ | 5 | <0.01 |
| Example 6 | ○ | 3 | <0.01 | ○ | 3 | <0.01 |
| Example 7 | ○ | 3 | <0.01 | ○ | 3 | <0.01 |
| Example 8 | ○ | 3 | <0.01 | ○ | 3 | <0.01 |
| Example 9 | ○ | 3 | <0.01 | ○ | 3 | <0.01 |
| Example 10 | ○ | 2 | 0.01 | ○ | 3 | 0.01 |
| Example 11 | ○ | 2 | 0.01 | ○ | 5 | 0.01 |
| Example 12 | ○ | 2 | 0.01 | ○ | 3 | 0.01 |
| Comparative Example 1 | Δ | 1-2 | 0.01 | Δ | 17 | 0.3 |
| Comparative Example 2 | Δ | 1 | 0.01 | Δ | 4 | 0.3 |
| Comparative Example 3 | X | 10 | 0.01 | X | 11 | 0.2 |
| Comparative Example 4 | Δ | 5 | 0.03 | X | 12 | 0.2 |
| Comparative Example 5 | X | 8 | 0.03 | X | 15 | 0.2 |
| Comparative Example 6 | X | 4 | 0.01 | X | 18 | 0.04 |
| Comparative Example 7 | X | 3 | 0.01 | X | >30 | 0.15 |
| Comparative Example 8 | Δ | 2 | 0.02 | X | 20 | 0.2 |
| Comparative Example 9 | Δ | 2 | 0.08 | X | >30 | 0.3 |

TABLE 1-continued

|  | Immediately after preparation | | | After standing at 54° C. for 14 days | | |
| --- | --- | --- | --- | --- | --- | --- |
|  | Self-dispersibility | Number of tube inversions | Sediment volume (30 min) | Self-dispersibility | Number of tube inversions | Sediment volume (30 min) |
| Comparative Example 10 | X | 3 | 0.01 | X | >30 | 0.15 |
| Comparative Example 11 | X | 2 | 0.04 | X | 8 | 0.3 |
| Comparative Example 12 | ○ | 3 | <0.01 | X | 5 | 0.25 |
| Comparative Example 13 | ○ | 3 | 0.01 | X | 10 | 0.3 |

INDUSTRIAL APPLICABILITY

As described above, the pesticidal composition of the present invention not only shows high wettability and dispersibility during the preparation of a pesticide solution, but also allows reduced sedimentation and easy preparation of a pesticide solution. Moreover, its dilution properties substantially remain unchanged over time. When sprayed over field crops, the pesticide solution is adsorbed evenly onto the crops to ensure stable control of organisms.

The invention claimed is:

1. A granulated pesticidal composition comprising a pesticidal active ingredient, a sodium lignosulfonate surfactant with a degree of sulfonation between 4.0 to 4.7 in an amount of 1 to 15% by weight of the total composition, a sulfate or phosphate salt of a polyoxyalkylene arylphenyl ether in an amount of 0.01 to 15% by weight of the total composition, potassium chloride and urea; wherein the sulfate or phosphate salt of the polyoxyalkylene arylphenyl ether is selected from the group consisting of a polyoxyethylene tristyrylphenyl ether sulfate salt and a polyoxyethylene tristyrylphenyl ether phosphate salt and wherein the pesticidal active ingredient comprises cyflufenamid and/or triflumizole.

2. A composition according to claim 1, wherein the ingredients contained in the composition were mixed and pulverized.

* * * * *